(12) United States Patent
Radulovacki et al.

(10) Patent No.: US 6,555,564 B1
(45) Date of Patent: Apr. 29, 2003

(54) NEUROPHARMACOLOGICAL TREATMENTS OF SLEEP-RELATED BREATHING DISORDERS

(75) Inventors: Miodrag Radulovacki, Chicago, IL (US); David W. Carley, Evanston, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/914,900

(22) PCT Filed: Mar. 3, 2000

(86) PCT No.: PCT/US00/05834

§ 371 (c)(1),
(2), (4) Date: Nov. 6, 2001

(87) PCT Pub. No.: WO00/51590

PCT Pub. Date: Sep. 8, 2000

Related U.S. Application Data

(60) Provisional application No. 60/122,846, filed on Mar. 4, 1999.

(51) Int. Cl.[7] ............................................. A61K 31/425
(52) U.S. Cl. ........................................................ 514/367
(58) Field of Search .......................................... 514/367

(56) References Cited

U.S. PATENT DOCUMENTS

| | | | |
|---|---|---|---|
| 5,075,290 A | | 12/1991 | Findley et al. |
| 5,182,386 A | * | 1/1993 | Albaugh et al. ............. 540/350 |
| 5,240,948 A | * | 8/1993 | Gueremy et al. ............ 514/367 |
| 5,356,934 A | | 10/1994 | Robertson et al. |
| 5,688,826 A | * | 11/1997 | Massey et al. ............... 514/443 |
| 5,728,728 A | * | 3/1998 | Kozachuk ..................... 514/483 |
| 6,121,265 A | * | 9/2000 | Treiber et al. ............... 514/250 |
| 6,124,361 A | * | 9/2000 | Chenard ....................... 514/561 |
| 6,136,861 A | * | 10/2000 | Chenard ....................... 514/361 |

FOREIGN PATENT DOCUMENTS

| | | |
|---|---|---|
| WO | WO 00/51590 | 9/2000 |

OTHER PUBLICATIONS

Hedner et al, Sleep, vol. 19(4), pp. 287–289, 1996.*
Hudgel et al, Am. J. Respir. Crit. Care Med., vol. 158, pp. 691–699, 1998.*
Dutschmann et al, J. Physiology, vol. 510(3), pp. 793–804, 1998.*
Dutschmann et al, Society for Neutoscience Abstracts, vol. 23(1–2), p. 725, 1997.*
Bennington et al., "Methodology: Scoring and Computerized Methods—Scoring Transitions to REM Sleep in Rats Based on the EEG Phenomena of Pre–REM Sleep: An Improved Analysis of Sleep Structure," *Sleep*, 17:28–36 (1994).
Botez et al., "Can We Treat Respiratory Failure in Friedreich Ataxia?" *Archives of Neurology*, 54(8):1030–1033 (1997).
Chamberlin et al., "A Brainstem Network Mediating Apneic Reflexes in the Rat," *J. Neuroscience*, 18(15):6048–6056 (1998).
Dutschmann et al., "NMDA and $GABA_A$ receptors in the rat Kölliker–Fuse area control cardiorespiratory responses evoked by trigeminal ethmoidal nerve stimulation," *J. Physiol.*, 510(3):793–804 (1998).
Dutschmann et al., "NMDA– and $GABA_A$–Receptors Relay Trigeminally Induced Apnoea and Cardiac Responses In The Rat Kolliker–Fuse Nucleus," *Society for Neuroscience Abstracts*, 23(1–2):725 (1997) (Abstract 285.6).
Feldman et al., "Neural Control of Breathing," In Developmental Neuroscience, Chapter 40, Academic Press, pp. 1063–1090 (1999).
Hedner et al., "A Double–Blind, Randomized Trial of Sabeluzole–A Putative Glutamate Antagonist–in Obstructive Sleep Apnea," *Sleep*, 19(4):287–9 (1996).
Hudgel et al., "Pharmacologic Treatment of Sleep–disordered Breathing," *American J. Respiratory and Critical Care Medicine*, 158(3):691–699 (1998).
Hudgel, "Pharmacologic Treatment of Obstructive Sleep Apnea," *J. Lab. Clin. Med.*, 126:13–18 (1995).
Iber et al., In Chapter VI "Ventilatory Control and Distrubances During Wakefulness and Sleep," Scientific American, Inc., pp. 1–14 (1997).
Monti et al., "Adenosine Analogues Modulate the Incidence of Sleep Apneas in Rats," *Pharamacol. Biochem. Behav.*, 51:125–131 (1995).
Chapter 42, "Regulation of Respiration," pp. 504–515.
International Search Report, PCT/US00/05834, European Patent Office Examination Authority.

* cited by examiner

Primary Examiner—James H. Reamer
(74) *Attorney, Agent, or Firm*—Marshall, Gerstein & Borun

(57) ABSTRACT

The present invention relates generally to pharmacological methods for the prevention or amelioration of sleep-related breathing disorders via administration of agents or combinations of agents that possess glutamate-related and/or glycine-related pharmacological activity or that modulate the release of either glutamate or glycine (or both) from nerve terminals with the central nervous system.

6 Claims, 4 Drawing Sheets

NEUROPHARMACOLOGICAL TREATMENTS OF SLEEP-RELATED BREATHING DISORDERS

This application claims priority to U.S. Provisional Application No. 60/122,846, filed Mar. 4, 1999, which is incorporated herein by reference in its entirety.

BACKGROUND OF THE INVENTION

1. Field of the Invention

This invention generally relates to methods for the pharmacological treatment of breathing disorders and, more specifically, to the administration of agents or combinations of agents having glutamate-related receptor activity and/or glycine-related receptor activity or activity that interferes with the release if either glutamate or glycine for the alleviation of steep apnea (central and obstructive) and other sleep-related breathing disorders.

2. Related Technology

Over the past several years much effort has been devoted to the study of a discrete group of breathing disorders that occur primarily during sleep with consequences that may persist throughout the waking hours in the form of sleepiness, thereby manifesting itself into substantial economic loss (e.g., thousands of lost man-hours) or employment safety factors (e.g., employee non-attentiveness during operation of heavy-machinery). Sleep-related breathing disorders are characterized by repetitive reduction in breathing (hypopnea), periodic cessation of breathing (apnea), or a continuous or sustained reduction in ventilation.

In general sleep apnea is defined as an intermittent cessation of airflow at the nose and mouth during sleep. By convention, apneas of at least 10 seconds in duration have been considered important, but in most individuals the apneas are 20–30 seconds in duration and may be as long as 2–3 minutes. While there is some uncertainty as to the minimum number of apneas that should be considered clinically important, by the time most individuals come to attention of the medical community they have at least 10 to 15 events per hour of sleep.

Sleep apneas have been classified into three types: central, obstructive, and mixed. In central sleep apnea the neural drive to all respiratory muscles is transiently abolished. In obstructive sleep apneas, airflow ceases despite continuing respiratory drive because of occlusion of the oropharyngeal airway. Mixed apneas, which consist of a central apnea followed by an obstructive component, are a variant of obstructive sleep apnea. The most common type of apnea is obstructive sleep apnea.

Obstructive sleep apnea syndrome (OSAS) has been identified in as many as 24% of working adult men and 9% of similar women, with peak prevalence in the sixth decade. Habitual heavy snoring, which is an almost invariant feature of OSAS, has been described in up to 24% of middle aged men, and 14% of similarly aged women, with even greater prevalence in older subjects.

Obstructive sleep apnea syndrome's definitive event is the occlusion of the upper airway, frequently at the level of the oropharynx. The resultant apnea generally leads to a progressive-type asphyxia until the individual is briefly aroused from the sleeping state, thereby restoring airway patency and thus restoring airflow.

An important factor that leads to the collapse of the upper airway in OSAS is the generation of a critical subatmospheric pressure during the act of inspiration that exceeds the ability of the airway dilator and abductor muscles to maintain airway stability. Sleep plays a crucial role by reducing the activity of the muscles of the upper airways including the dilator and abductor muscles.

In most individuals with OSAS the patency of the airway is also compromised structurally and is therefore predisposed to occlusion. In a minority of individuals the structural compromise is usually due to obvious anatomic abnormalities, i.e, adenotonsillar hypertrophy, retrognathia, or macroglossia. However, in the majority of individuals predisposed to OSAS, the structural abnormality is simply a subtle reduction in airway size, i.e., "pharyngeal crowding." Obesity also frequently contributes to the reduction in size seen in the upper airways. The act of snoring, which is actually a high-frequency vibration of the palatal and pharyngeal soft tissues that results from the decrease in the size of the upper airway lumen, usually aggravates the narrowing via the production of edema in the soft tissues.

The recurrent episodes of nocturnal asphyxia and of arousal from sleep that characterize OSAS lead to a series of secondary physiologic events, which in turn give rise to the clinical complications of the syndrome. The most common manifestations are neuropsychiatric and behavioral disturbances that are thought to arise from the fragmentation of sleep and loss of slow-wave sleep induced by the recurrent arousal responses. Nocturnal cerebral hypoxia also may play an important role. The most pervasive manifestation is excessive daytime sleepiness. OSAS is now recognized as a leading cause of daytime sleepiness and has been implicated as an important risk factor for such problems as motor vehicle accidents. Other related symptoms include intellectual impairment, memory loss, personality disturbances, and impotence.

The other major manifestations are cardiorespiratory in nature and are thought to arise from the recurrent episodes of nocturnal asphyxia. Most individuals demonstrate a cyclical slowing of the heart during the apneas to 30 to 50 beats per minute, followed by tachycardia of 90 to 120 beats per minute during the ventilatory phase. A small number of individuals develop severe bradycardia with asystoles of 8 to 12 seconds in duration or dangerous tachyarrhythmias, including unsustained ventricular tachycardia. OSAS also aggravates left ventricular failure in patients with underlying heart disease. This complication is most likely due to the combined effects of increased left ventricular afterload during each obstructive event, secondary to increased negative intrathoracic pressure, recurrent nocturnal hypoxemia, and chronically elevated sympathoadrenal activity.

Central sleep apnea is less prevalent as a syndrome than OSAS, but can be identified in a wide spectrum of patients with medical, neurological, and/or neuromuscular disorders associated with diurnal alveolar hypoventilation or periodic breathing. The definitive event in central sleep apnea is transient abolition of central drive to the ventilatory muscles. The resulting apnea leads to a primary sequence of events similar to those of OSAS. Several underlying mechanisms can result in cessation of respiratory drive during sleep. First are defects in the metabolic respiratory control system and respiratory neuromuscular apparatus. Other central sleep apnea disorders arise from transient instabilities in an otherwise intact respiratory control system.

Many healthy individuals demonstrate a small number of central apneas during sleep, particularly at sleep onset and in REM sleep. These apneas are not associated with any physiological or clinical disturbance. In individuals with clinically significant central sleep apnea, the primary sequence of events that characterize the disorder leads to prominent physiological and clinical consequences. In those individuals with central sleep apnea alveolar hypoventilation syndrome, daytime hypercapnia and hypoxemia are usually evident and the clinical picture is dominated by a history of recurrent respiratory failure, polycythemia, pulmonary hypertension, and right-sided heart failure. Complaints of sleeping poorly, morning headache, and daytime fatigue and sleepiness are also prominent. In contrast, in individuals whose central sleep apnea results from an instability in respiratory drive, the clinical picture is dominated by features related to sleep disturbance, including recurrent nocturnal awakenings, morning fatigue, and daytime sleepiness.

Currently, the most common and most effective treatment, for adults with sleep apnea and other sleep-related breathing disorders are mechanical forms of therapy that deliver positive airway pressure (PAP). Under PAP treatment, an individual wears a tight-fitting plastic mask over the nose when sleeping. The mask is attached to a compressor, which forces air into the nose creating a positive pressure within the patient's airways. The principle of the method is that pressurizing the airways provides a mechanical "splinting" action, which prevents airway collapse and therefore, obstructive sleep apnea. Although an effective therapeutic response is observed in most patients who undergo PAP treatment, many patients cannot tolerate the apparatus or pressure and refuse treatment. Moreover, recent covert monitoring studies clearly demonstrate that long-term compliance with PAP treatment is very poor.

A variety of upper airway and craniofacial surgical procedures have been attempted for treatment of OSAS. Adenotonsillectomy appears to be an effective cure for OSAS in many children, but upper airway surgery is rarely curative in adult patients with OSAS. Surgical "success" is generally taken to be a 50% reduction in apnea incidence and there are no useful screening methods to identify the individuals that would benefit from the surgery versus those who would not derive a benefit.

Pharmacological treatments of several types have been attempted in patients with sleep apnea but, thus far, none have proven to be generally useful. A recent systematic review of these attempts is provided by Hudgel [*J. Lab. Clin. Med.*, 126:13–18 (1995)]. A number of compounds have been tested because of their expected respiratory stimulant properties. These include (1) acetazolamide, a carbonic anhydrase inhibitor that produced variable improvement in individuals with primary central apneas but caused an increase in obstructive apneas, (2) medroxyprogesterone, a progestin that has demonstrated no consistent benefit in OSAS, and (3) theophylline, a compound usually used for the treatment of asthma, which may benefit patients with central apnea but appears to be of no use in adult patients with obstructive apnea.

Other attempted pharmacological treatment includes the administration of adenosine, adenosine analogs and adenosine reuptake inhibitors (U.S. Pat. No. 5,075,290). Specifically, adenosine, which is a ubiquitous compound within the body and which levels are elevated in individuals with OSAS, has been shown to stimulate respiration and is somewhat effective in reducing apnea in an animal model of sleep apnea.

Other possible pharmacological treatment options for OSAS include agents that stimulate the brain activity or are opioid antagonists. Specifically, since increased cerebral spinal fluid opioid activity has been identified in OSAS, it is a logical conclusion that central stimulants or opioid antagonists would be a helpful treatment of OSAS. In reality, doxapram, which stimulates the central nervous system and carotid body chemoreceptors, was found to decrease the length of apneas but did not alter the average arterial oxygen saturation in individuals with obstructive sleep apnea. The opioid antagonist naloxone, which is known to stimulate ventilation was only slightly helpful in individuals with obstructive sleep apnea.

Because OSAS is strongly correlated with the occurrence of hypertension, agents such as angiotensin-converting enzyme (ACE) inhibitors may be of benefit in treating OSAS individuals with hypertension but this does not appear to be a viable treatment for OSAS itself.

Finally, several agents that act on neurotransmitters and neurotransmitter systems involved in respiration have been tested in individuals with OSAS. Most of these compounds have been developed as anti-depressant medications that work by increasing the activity of monoamine neurotransmitters including norepinephrine, dopamine, and serotonin. Protriptyline, a tricyclic anti-depressant has been tested in several small trials with variable results and frequent and significant side effects. As serotonin may promote sleep and stimulate respiration, tryptophan, a serotonin precursor and selective serotonin reuptake inhibitors have been tested in individuals with OSAS. While a patent has been issued for the use of the serotonin reuptake inhibitor, fluoxetine (U.S. Pat. No. 5,356,934), initial evidence suggests that these compounds may yield measurable benefits in only approximately 50% of individuals with OSAS. Therefore in view of the fact that the only viable treatment for individuals suffering from sleep-related breathing disorders is a mechanical form of therapy (PAP) for which patient compliance is low, and that hopes for pharmacological treatments have yet to come to fruition, there remains a need for simple pharmacologically-based treatments that would offer benefits to a broad base of individuals suffering from a range of sleep-related breathing disorders. There also remains a need for a viable treatment of sleep-related breathing disorders that would lend itself to a high rate of patient compliance.

SUMMARY OF THE INVENTION

The invention is directed to providing pharmacological treatments for the prevention or amelioration of sleep-related breathing disorders.

The present invention is directed to methods for the prevention or amelioration of sleep-related breathing disorders, the method comprising the administration of an effective dose of a central nervous system glutamate receptor antagonist or glycine receptor antagonist to a patient in need of such therapy, alone or in a combination comprising a glutamate receptor antagonist and a glycine receptor antagonist. The present invention is also directed to methods comprising the administration of an agent or combination of agents that exhibit both glutamate receptor antagonism and glycine receptor antagonism in the central nervous system for the prevention or amelioration of sleep-related breathing disorders.

The present invention is further directed to methods comprising the administration of an agent or combination of agents that inhibit the release of glutamate or glycine within the central nervous system for the prevention or amelioration of sleep-related breathing disorders. The invention is also directed to agents or combinations of agents that inhibit the release of both glycine and glutamate within the central nervous system.

The present invention is also directed to methods comprising the administration of agents having agonistic activity at presynaptic inhibitory receptors for glutamatergic/glycinergic terminals within the central nervous system for the prevention or amelioration of sleep-related breathing disorders. The present invention is further directed to agents that inhibit the reuptake of agonists at presynaptic inhibitory receptors for glutamatergic/glycinergic terminals within the central nervous system for the prevention or amelioration of sleep-related breathing disorders.

Routes of administration for the foregoing methods may be by any systemic means including oral, intraperitoneal, subcutaneous, intravenous, intramuscular, transdermal, or by other routes of administration. Osmotic mini-pumps and timed-released pellets or other depot forms of administration may also be used. The only limitation being that the route of administration results in the ultimate delivery of the pharmacological agent to the appropriate receptor.

Sleep-related breathing disorders include, but are not limited to, obstructive sleep apnea syndrome, apnea of prematurity, congenital central hypoventilation syndrome, obesity hypoventilation. syndrome, central sleep apnea syndrome, Cheyne-Stokes respiration, and snoring.

Exemplary glycine receptor antagonists include, but are not limited to 5,7-dichlorokynurenate (NMDA receptor glycine site), L689560 (NMDA receptor glycine site; trans-2-carboxy,5,7-dichloro-4-phenylaminocarbonylamino-1,2,3,4-tetrahydro-quinoline), MNQX (NMDA receptor glycine site; 6-8-dinitroquinoxaline-2,3-dione), picrotoxin, and cyanotriphenylborate.

Exemplary glutamate receptor antagonists include, but are not limited to D-AP5 (D(-)-2-amino-5-phosphonopentanoate), CGS19755 (4-phosphonomethyl-2-piperidine carboxylic acid), CGP37849 (D,L-(E)-2-amino-4-methylphosphono-3-pentanoic acid), LY233053 (cis-(±)-4-(2H-tetrazol-5-yl)methyl-piperidine-2-carboxyl acid), AIDA (1-aminoindan-1,5(RS)-dicarboxylic acid), (s)-(+)-CBPG ((s)-(+)-2-(3'-carboxy-bicyclo(1.1.1.)pentyl) glycine), CPCCOEt (cyclopropan(b)chromen-1a-carboxylate), EGLU ((s)-(α)-ethylglutamate), LY307452 (2s,4s-2-amino-4-(4,4-diphenylbut-1-yl)pentan-1,5-dioc acid), LY341495 (2s-2-amino-2-(1s,2s-2-carboxy-cyclopropan-1-yl)-3-(xanth-9-yl)propanoic acid), PCCG-4 (2s,1's,2's,3'R)-2-(2'-carboxy-3'-phenylcyclo-propyl) glycine), 4-CPG (4-carboxyphenylglycine), memantine, and amantadine.

Exemplary GABA receptor agonists (presynaptic inhibitors at glutamatergic/glycinergic nerve terminals within the central nervous system) include, but are not limited to isoguvacine, muscimol, THIP, piperidine-4-sulphonic acid, flunitrazepam, zolpidem, abecarnil, ZK93423, L-baclofen, CGP27492, piracetam, progabide, and CGP35024.

Exemplary inhibitors of glutamate release include, but are not limited to, lamotrigine, BW1003C87, and riluzole.

DETAILED DESCRIPTION OF THE INVENTION

Figure 1:
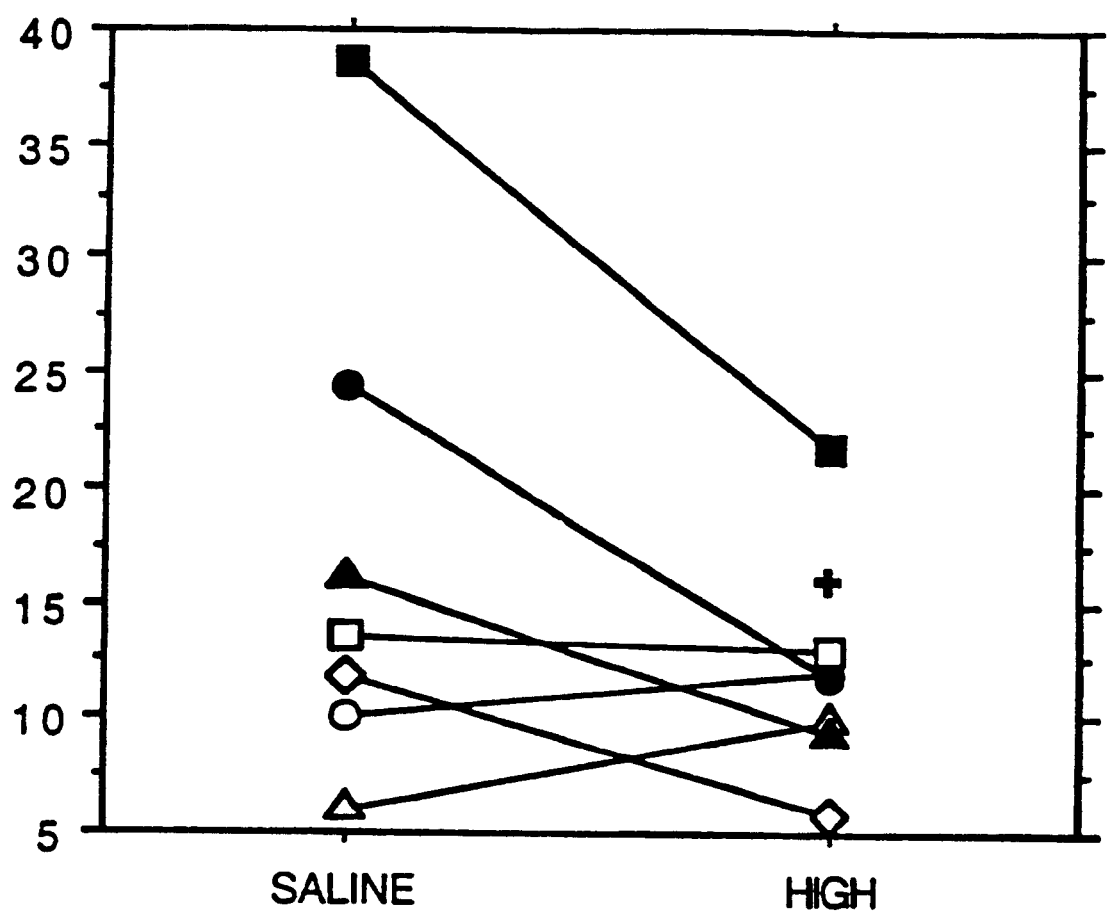
FIG. 1 illustrates the effect of riluzole, an inhibitor of glutamate release, on the expression of spontaneous apneas of seven different animals (rats) during non-rapid eye movement (NREM) sleep. The ordinate represents apneas per hour of NREM sleep observed during six hour recordings. Fifteen minutes prior to each recording, each animal received a 1 ml/kg bolus injection (intraperitoneal) of either saline (left column of points) or a 4.0 mg/kg riluzole (right column of points: High).

The central nervous system controls breathing by generating the motor outflow driving the rhythmic contraction and relaxation of respiratory pump muscles and by modulating the tone of skeletal and smooth muscles in the upper airways and bronchi to control resistance to air flow. Specifically, the central nervous system drives respiratory muscles to produce ventilation appropriate for the regulation of blood $O_2$ and $CO_2$ adaptable over an order of magnitude range in metabolic demand. In controlling breathing, the central nervous system must also compensate for wide ranges of body posture and movement, which affect lung and musculoskeletal mechanics and may compromise muscle or cardiopulmonary function. This control of ventilation must continue from birth until death without lapses of more than a few minutes.

The drive for continuous ventilation is strong. Typically, breathing is the last consequential movement to disappear following generalized depression of higher function, such as during surgical anesthesia or following insults to the brain (e.g., hypoglycemic coma). Automatic, homeostatic breathing can remain in people who have lost cortical function.

Ventilation requires a patterned motor output with appropriate timing and magnitude of muscle contraction and relaxation and coordination of this activity among synergists and antagonists; that is, the muscles that move the rib cage in and out and the diaphragm up and down either pull together (synergistic muscles) or pull in opposite directions (opposing muscles). Ventilation is controlled by a complex and mutable regulatory system composed of many distinct components. The brainstem and spinal cord contain the basic circuits for rhythm generation and pattern formation and are targets of relevant sensory afferents. Suprapontine structures, including the cortex, hypothalamus, and cerebellum, affect ventilation but are not essential, as decerebrate mammals continue to breathe with appropriate blood gas regulation. Sensory afferents are essential for regulation, but also are not required for basic respiratory pattern formation Following paralysis (or deafferentation), provided that blood gas homeostasis is maintained by artificial means (e.g., mechanical ventilation), rhythmic motor output continues in nerves innervatiung respiratory muscles.

It is believed that a simple rhythm-generating system in the brainstem lies at the core of the neural circuits for breathing. The respirator center of the brainstem is composed of several widely dispersed groups of neurons located bilaterally in the medulla oblongata and pons. It is divided into three major collections of neurons: (1) a dorsal respiratory group, located in the dorsal portion of the medulla, which mainly causes inspiration, (2) a ventral respiratory group, located in the ventrolateral part of the medulla, which may cause either expiration or inspiration, depending upon which neurons in the group are stimulated, and (3) the pneumotaxic center, located dorsally in the superior portion of the pons, which helps control both the rate and pattern of breathing. The dorsal respiratory group of neurons plays the fundamental role in the control of respiration.

Within the brainstem, amino acid neurotransmission (i.e., glutamate, glycine) is fundamental in the communication between respiratory neurons. Such transmission is essential for rhythm generation. The precise role amino acids play in generating respiratory rhythm is unknown, but may include providing, the tonic background excitatory drive that is required to bring various populations of respiratory neurons to threshold. Amino acids also may contribute to recurrent excitatory connections that build up activity within the network. Alternatively, these amino acids might coordinate the periods of excitation in neurons contributing to rhythm generation, thereby providing the conditions necessary for the initiation of bursting in conditional pacemaker neurons.

Previous studies demonstrated that administration of the excitatory amino acid glutamate into the. brainstem provoked reflex apneas [Chamberlin et al., *J. Neurosci.* 18(15) :6048–6056; 1998]. Specifically, administration (of the amino acid) into the intertrigeminal region of the brainstem provoked reflexive apneas, a critical response for protecting the airways from aspiration of food/liquids.

The following examples describe methods that are used to assess the ability of agents or combinations of agents having glutamate-related receptor antagonistic activity and/or glycine-related receptor antagonistic activity or activity that interferes with the release of either glutamate or glycine for the alleviation of sleep apnea (central and obstructive) and other sleep-related breathing disorders. The following examples further illustrate agents or combinations of agents having glutamate-related receptor activity and/or glycine-related receptor activity or activity that interferes with the release of either glutamate or glycine that may be used to effectively suppress or prevent sleep-related breathing disorders.

Example 1 describes the model for treatment with either agents or combinations of agents having glutamate-related receptor antagonistic activity and/or glycine-related receptor antagonistic activity or activity that interferes with the release of either glutamate or glycine and subsequent physiological recording and testing.

Example 2 describes the methods for the physiological recording of treatment and control animals and subsequent to administration of either glutamate-related receptor antagonistic activity and/or glycine-related receptor antagonistic activity or activity that interferes with the release of either glutamate or glycine.

Example 3 described the results obtained from the administration of riluzole on the expression of spontaneous sleep apneas both in NREM and REM sleep.

Example 4 describes agents or combinations of agents having glutamate-related receptor antagonistic activity and/ or glycine-related receptor antagonistic activity or activity that interferes with the release of either glutamate or glycine that are used to effectively suppress or prevent sleep-related breathing disorders.

The following examples are illustrative of aspects of the present invention but are not to be construed as limiting.

EXAMPLE 1

Preparation of Animals for Physiological Testing and Recording

Adult, male Sprague-Dawley rats (Sasco-King, Wilmington, Mass.; usually 8 per test group; 300 g) are maintained on a 12-hour light (08:00–20:00 hour)/12-hour dark (20:00–08:00 hour) cycle for one week, housed in individual cages and given ad libitum access to food and water. Following the one week of acclimatization, animals are subjected to the following surgical procedures.

Acclimatized animals are anesthetized for the implantation of cortical electrodes for electroencephalogram (EEG) recording and neck muscle electrodes for electromyogram (EMG) recording using a mixture of ketamine (Vedco, Inc., St. Joseph, Mo.; 100 mg/ml) and acetylpromazine (Vedco, Inc., St. Joseph, Mo.; 10 mg/ml; 4:1, volume/volume) at a volume of 1 ml/kg body weight. The surface of the skull is exposed surgically and cleaned with a 20% solution of hydrogen peroxide followed by a solution of 95% isopropyl alcohol. Next, a dental preparation of sodium fluoride (Flura-GEL®, Saslow Dental, Mt. Prospect, Ill.) is applied to harden the skull above the parietal cortex and allowed to remain in place for 5 minutes. The fluoride mixture is then removed from the skull above the parietal cortex. The EEG electrodes consisting of four stainless steel machine screws, having leads attached thereto, are threaded into the skull to rest on the dura over the parietal cortex. A thin layer of Justi® resin cement (Saslow Dental, Mt. Prospect, Ill.) is applied to cover the screw heads (of screws implanted in the skull) and surrounding skull to further promote the adhesion of the implant. EMG electrodes consisting of two ball-shaped wires are inserted into the bilateral neck musculature. All leads (i.e., EEG and EMG leads) are soldered to a miniature connector (39F1401, Newark Electronics, Schaumburg, Ill.). Lastly, the entire assembly is fixed to the skull with dental cement.

Further, if central administration (rather than systemic administration) of the agents or combinations of agents having glutamate-related receptor activity and/or glycine-related receptor activity is desired, using the appropriate coordinates, a cannula is stereotaxically implanted within a specified region of the animal's brainstem.

After surgery, all animals are allowed to recover for one week before being subjected to another surgery that involved implantation of a radiotelemetry transmitter (TA11-PXT, Data Sciences International, St. Paul, Minn.) for monitoring blood pressure (BP) and heart period (HP), estimated as pulse interval. After the animals are anesthetized (as described above), the hair from the subxiphoid space to the pelvis is removed. The entire area is scrubbed with iodine and rinsed with alcohol and saline. A 4–6 cm midline abdominal incision is made to allow good visualization of the area from the bifurcation of the aorta to the renal arteries. A retractor is used to expose the contents of the abdomen and the intestine is held back using saline moistened gauze sponges. The aorta is dissected from the surrounding fat and connective tissues using sterile cotton applicators. A 3-0 silk suture is placed beneath the aorta and traction is applied to the suture to restrict the blood flow. Then the implant (TA11-PXT) is held by forceps while the aorta is punctured just cranial to the bifurcation using a 21-gauge needle bent at the beveled end. The tip of the catheter is inserted under the needle using the needle as a guide until the thin-walled BP sensor section is within the vessel. Finally, one drop of tissue adhesive (Vetbond,®, 3M, Minneapolis, Minn.) is applied to the puncture site and covered with a small square of cellulose fiber (approximately 5 $mm^2$) so as to seal the puncture after catheter insertion. The radio implant is attached to the abdominal wall by 3-0 silk suture, and the incision is closed in layers. After the second surgery, animals are again allowed a one week recovery period prior to administration of the either agents or combinations of agents having glutamate-related receptor activity and/or glycine receptor activity and subsequent physiological recording.

EXAMPLE 2

Physiological Recording and Suppression of Apneas

Physiological parameters (see below) from each animal are recorded on numerous occasions in random order, with recordings for an individual animal separated by at least 3 days. Fifteen minutes prior to each recording each animal receives a systemic injection (1 ml/kg intraperitoneal bolus injection) of either saline (control) or test agents or combinations of test agents (having glutamate-related receptor activity and/or glycine-related receptor activity or activity that interferes with the release of either glutamate or glycine or combinations of agents having glutamate-related receptor activity and/or glycine receptor activity). Polygraphic recordings are made from hours 10:00–16:00.

Respiration is recorded by placing each animal, unrestrained, inside a single chamber plethysmograph (PLYUN1R/U; Buxco Electronics, Sharon, Conn.; dimension 6 in.×10 in.×6 in.) ventilated with a bias flow of fresh room air at a rate of 2 L/min. A cable, plugged onto the animal's connector and passed through a sealed port, is used to carry the bioelectrical activity from the head implant. Respiration, blood pressure, EEG activity, and EMG activity are displayed on a video monitor and simultaneously digitized 100 times per second and stored on computer disk (Experimenter's Workbench; Datawave Technologies; Longmont, Colo.).

Sleep and waking states are assessed using the biparietal EEG and nuchal EMG signals on 10-second epochs as described by Bennington el al. [Sleep, 17:28–36 (1994)]. This software discriminates wakefulness (W) as a high frequency low amplitude EEG with a concomitant high EMG tone, NREM sleep by increased spindle and theta activity together with decreased EMG tone, and REM sleep by a low ratio of a delta to theta activity and an absence of EMG tone. Sleep efficiency is measured as the percentage of total recorded epochs staged as NREM or REM sleep.

An accepted physiological animal model [rat; Monti, et al., Pharmacol. Biochem. Behalf., 51:125–131 (1995)] of spontaneous sleep apnea is used to assess the effects of either agents or combinations of agents having glutamate-related receptor activity and/or glycine receptor activity. More specifically, spontaneous sleep apneas, defined as cessation of respiratory effort for at least 2.5 seconds, are scored for each recording session and are associated with the stage of sleep in which they occurr, NREM or REM sleep. The duration requirement of 2.5 seconds represents at least 2 "missed" breaths, which is therefore analogous to a 10 second apnea duration requirement in humans, which also reflects 2–3 missed breaths. The events detected represent central apneas because decreased ventilation associated with obstructed or occluded airways would generate an increased plethysmographic signal, rather than a pause. An apnea index (AI), defined as apneas per hour in a stage are separately determined for NREM and REM sleep. The effects of sleep stage (NREM vs. REM) and injection (control vs. (a) pharmacological agents exhibiting either glutamate or glycine receptor antagonism within the central nervous system, alone or in combination; (b) agents that exhibit both glutamate and glycine receptor antagonism within the central nervous system; (c) agents that inhibit the release of glutamate or glycine within the central nervous system, alone or in combination; (d) agents that inhibit both the release, of glycine and glutamate within the central nervous system; (e) agonists at presynaptic inhibitory (GABA) receptors for glutamatergic/glycinergic terminals within the central nervous system; or (f) agents that inhibit the reuptake of agonists at presynaptic inhibitory (GABA) receptors for glutamatergic/glycinergic terminals within the central nervous system) are tested using ANOVA with repeated measures. Multiple comparisons are controlled using Fisher's protected least significant difference (PLSD). In addition, the timing and volume of each breath are scored by automatic analysis (Experimenters' Workbench; Datawave Technologies, Longmont, Colo.). For each animal the mean respiratory rate (RR) and minute ventilation (MV) is computed for W throughout the 6 hour control recording and used as a baseline to normalize respiration during sleep and during GR38032F administration in that animal. One way ANOVA is also performed by non-parametric (Kruskal-Wallis) analysis.

Similar software (Experimenters' Workbench; Datawave Technologies, Longmont, Colo.) is employed to analyze the blood pressure waveform; for each beat of each recording, systolic (SBP) and diastolic (DBP) blood pressures and pulse interval are measured. The pulse interval provides a beat by beat estimate of HP. Mean BP (MBP) is estimated according to the weighted average of SBP and DBP for each beat: $MBP=DBP+(SBP-DBP)/3$. The parameters for each beat are also classified according to the sleep/wake state and recording hour during which they occurred.

EXAMPLE 3

Supression of Sleep Apneas

The ability of the administration of riluzole, which readily enters the central nervous system to act as an inhibitor of glutamate release, to inhibit spontaneous apneas was ascertained. Specifically, seven adult male Sprague-Dawley rats (Sasco-King, Wilmington, Mass.; 300–350 g) were maintained on a 12-h light (08:00–20:00 hour)/12-hour dark (20:00–08:00) cycle for one week, housed in individual cages, and given ad libitum access to food and water. Following the one week of acclimatization, animals were prepared for physiological testing via the surgical procedures (i.e., implantation of cortical electrodes for EEG recording and neck muscle electrodes for EMG recording, implantation of a radiotelemetry transmitter for BP and HP monitoring) as set forth above in Example 1. After completion of the surgical procedures, animals were allowed a one week recovery period prior to use in the present study.

Each animal was recorded on two occasions, with recordings for an individual animal separated by at least three days. Fifteen minutes prior to each recording, each animal received (via intraperitoneal injection), in random order, one of the following: (a) saline solution (control) or (b) 4.0 mg/kg riluzole.

Respiration BP, EEG, and EMG data were determined and recorded via the experimental procedure as specifically set forth above in Example 2. As in Example 2, sleep apneas, defined as cessation of respiratory effort for at least 2.5 s, were scored for each recording session and were associated with the stage in which they occurred: NREM or REM sleep. The duration requirement of 2.5 s represents at least two "missed" breaths, which is analogous to a 10-s apnea duration requirement in humans.

The effects of sleep stage (NREM vs REM) and injection (control vs. administration of riluzole ) on apnea indexes, respiratory pattern, BP, and HP were tested using analysis of variance (ANOVA) with repeated measures. Multiple comparisons were controlled using Fisher's protected leastsignificance difference (PLSD). One-way ANOVA was also performed by nonparametric (Kruskal-Wallis) analysis. Conclusions using parametric and nonparametric ANOVA were identical in all cases.

Results of the administration of either saline or riluzole on the expression of spontaneous apneas in NREM sleep during a 6 hour polygraphic recording is set forth in FIG. 1. Straight line segments connect observations from repeated recording in individual animals. During NREM sleep, administration of riluzole induced a decrease in apnea expression in 5 of 7 the animals tested.

Figure 3:
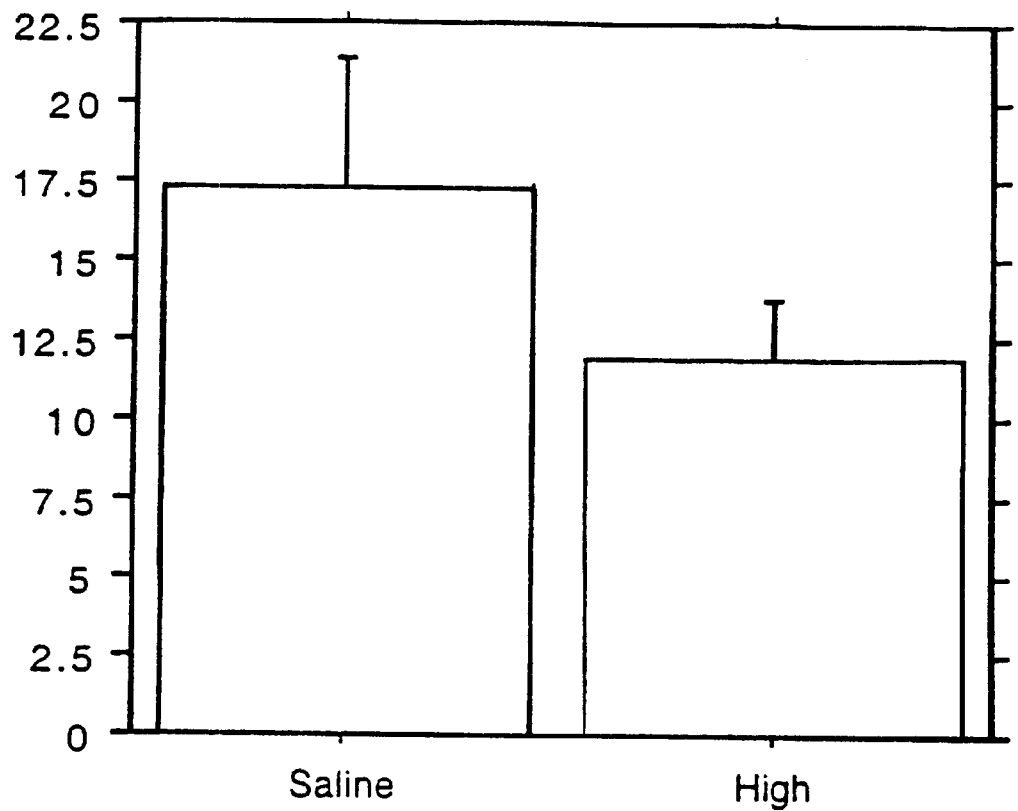
FIG. 3 sets forth mean apneas (± standard error) per hour of NREM sleep in the seven animals replotted from FIG. 1.

Results from FIG. 1 were replotted to obtain the mean apneas per hour during NREM sleep (FIG. 3). Analysis of variance with repeated measures demonstrated that the average decrease in apnea expression associated with riluzole administration (HIGH) was 31% (p=0.05).

Figure 2:
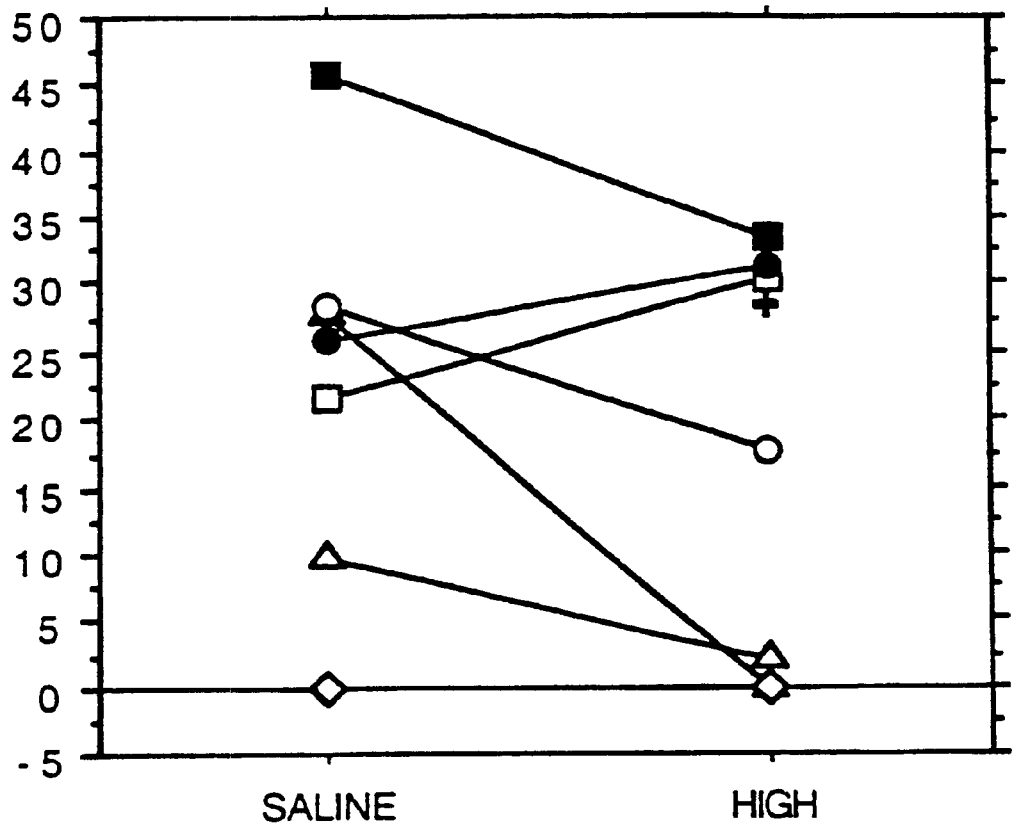
FIG. 2 illustrates the effect of riluzole on the expression of spontaneous apneas of seven animals (same animals as in FIG. 1) during rapid eye movement (REM) sleep. The ordinate represents apneas per hour of REM sleep observed during six hour recordings.

Results of the administration of either saline or riluzole on the expression of spontaneous apneas in REM sleep during a 6 hour polygraphic recording is set forth in FIG. 2. Straight line segments connect observations from repeated recording in individual animals. During REM sleep, apnea expression decreased or remained the same in 5 of 7 the animals tested.

Figure 4:
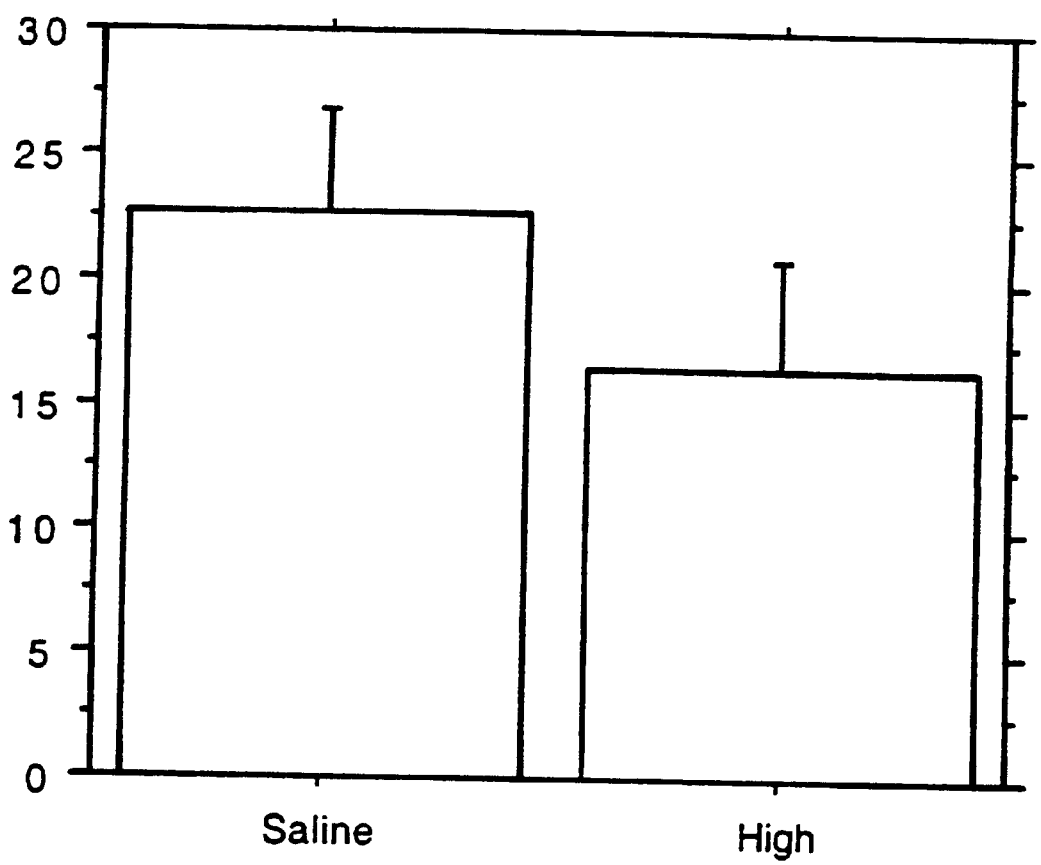
FIG. 4 sets forth mean apneas (± standard error) per hour of REM sleep in the seven animals replotted from FIG. 2.

Results from FIG. 2 were replotted to obtain the mean apneas per hour during REM sleep (FIG. 4). Analysis of variance with repeated measures demonstrated that the average decrease in apnea expression associated with riluzole administration (HIGH) was 27% (p=0.11).

Overall, the results presented herein indicate that administration of the glutamate release inhibitor, riluzole, induces a physiologically significant decrease in the production of spontaneous sleep apnease during both NREM and REM sleep.

EXAMPLE 3

Suppression or Prevention of Sleep Apneas

Sleep related breathing disorders (sleep apnea syndrome, apnea of infancy, Cheyne-Stokes respiration, sleep-related hypoventilation syndromes) may be effectively prevented or suppressed via systemic administration of (a) pharmacological agents exhibiting either glutamate or glycine receptor antagonism within the central nervous system, alone or in a combination comprising a glutamate receptor antagonist and a glycine receptor antagonist; (b) agents that exhibit both glutamate and glycine receptor antagonism within the central nervous system; (c) agents that inhibit the release of glutamate or glycine within the central nervous system, alone or in combination; (d) agents that inhibit both the release of glycine and glutamate within the central nervous system; (e) agonists at presynaptic inhibitory (GABA) receptors for glutamatergic/glycinergic terminals within the central nervous system; or (f) agents that inhibit the reuptake of agonists at presynaptic inhibitory (GABA) receptors for glutamatergic/glycinergic terminals within the central nervous system.

Specifically, an individual diagnosed with a sleep-related breathing disorder is administered either a composition or agent having any of the foregoing pharmacological profiles in an amount effective to prevent or suppress such disorders. The specific dose may be calculated according to such factors as body weight or body surface. Further refinement of the calculations necessary to determine the appropriate dosage for treatment of sleep-related breathing disorders is routinely made by those of ordinary skill in the art without undue experimentation. Appropriate dosages may be ascertained through use of established assays for determining dosages. Routes of administration for the foregoing methods may be by any systemic means including oral, intraperitoneal, subcutaneous, intravenous, intramuscular, transdermal, or by other routes of administration. Osmotic mini-pumps and timed-released pellets or other depot forms of administration may also be used.

Those of skill in the art will recognize that exemplary glycine receptor antagonists include, but are not limited to 5,7-dichlorokynurenate (NMDA receptor glycine site), L689560 (NMDA receptor glycine site), MNQX (NMDA receptor glycine site), picrotoxin, and cyanotriphenylborate.

Those of skill in the art will also recognize that exemplary glutamate receptor antagonists include, but are not limited to D-AP5, CGS19755, CGP37849, LY233053, AIDA, (s)-(+)-CBPG, CPCCOEt, EGLU, LY307452, LY341495, PCCG-4, 4CPG, and MPPG.

Those of skill in the art will further recognize that exemplar GABA agonists (presynaptic inhibitors at glutamatergic/glycinergic nerve terminals within the central nervous system) include, but are not limited to isoguvacine, muscimol, THIP, piperidine-4-sulphonic acid, flunitrazepam, zolpidem, abecarnil, ZK93423, L-baclofen, CGP27492, piracetam, progabide, and CGP35024.

Those of skill in the art will also recognize that exemplary inhibitors of glutamate release include, but are not limited to, lamotrigine, BW1003C87, and riluzole.

Finally, those of skill in the art will recognize that with respect to the compounds discussed above, such compounds may contain a center of chirality. Thus such agents may exist as different enantiomers of enantiomeric mixtures. Use of any one enantiomer alone or contained within an enantiomeric mixture with one or more stereoisomers is contemplated by the present invention.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements. All literature cited herein is incorporated by reference.

What is claimed is:

1. A method of preventing or ameliorating sleep-related breathing disorder the method comprising administering to a patient in need thereof an effective amount of a glutamate receptor antagonist wherein the effects of the antagonist are exerted only in the central nervous system.

2. The method of claim 1 wherein the sleep-related breathing disorder is selected from the group consisting of obstructive sleep apnea syndrome, apnea of prematurity, congenital central hypoventilation syndrome, obesity hypoventilation syndrome, central sleep apnea syndrome, Cheyne-Stokes respiration, and snoring.

3. The method of claim 1 wherein the glutamate receptor antagonist is selected from the group consisting of D-AP5, CGS19755, CGP37849, LY233053, AIDA, (s)-(+)-CBPG, CPCCOEt, EGLU, LY307452, LY341495, PCCG-4, 4CPG, memantine, and amantadine.

4. A method of preventing or ameliorating sleep-related breathing disorders the method comprising administering to a patient in need thereof an effective amount of an agent or combination of agents that inhibit the release of glutamate from nerve terminals within the central nervous system.

5. The method of claim 4 wherein the sleep-related breathing disorder is selected from the group consisting of obstructive sleep apnea syndrome, apnea of prematurity, congenital central hypoventilation syndrome, obesity hypoventilation syndrome, central sleep apnea syndrome, Cheyne-Stokes respiration, and snoring.

6. The method of claim 2 wherein the glutamate receptor antagonist is selected from the group consisting of D-AP5, CGS19755, CGP37849, LY233053, AIDA, (s)-(+)-CBPG, CPCCOEt, EGLU, LY307452, LY341495, PCCG-4, 4CPG, memantine, and amantadine.

* * * * *

UNITED STATES PATENT AND TRADEMARK OFFICE
CERTIFICATE OF CORRECTION

PATENT NO. : 6,555,564 B1  
DATED : April 29, 2003  
INVENTOR(S) : Miodrag Radulovacki et al.

It is certified that error appears in the above-identified patent and that said Letters Patent is hereby corrected as shown below:

Column 7,  
Line 6, "providing," should be -- providing --  
Line 15, "the." should be -- the --

Column 8,  
Line 57, "Vetbond,®," should be -- Vetbond®, --

Column 9,  
Line 41, "*Behalf.,*" should be -- *Behav.* --  
Line 66, "release," should be -- release --

Signed and Sealed this

Second Day of March, 2004

JON W. DUDAS  
*Acting Director of the United States Patent and Trademark Office*